United States Patent [19]

Bloomfield, III

[11] Patent Number: 4,691,360
[45] Date of Patent: Sep. 1, 1987

[54] VOICE SIMULATOR

[76] Inventor: John W. Bloomfield, III, 19 Oyster Landing, Hilton Head Island, S.C. 29938

[21] Appl. No.: 802,585

[22] Filed: Nov. 26, 1985

[51] Int. Cl.$^4$ ............................................. A61F 1/20
[52] U.S. Cl. .......................................... 381/70; 623/9
[58] Field of Search ............. 381/70; 623/9; 446/204, 446/207, 415, 448

[56] References Cited

U.S. PATENT DOCUMENTS

| 2,202,467 | 5/1940 | Riesz | 381/70 |
| 3,914,550 | 10/1975 | Cardwell, Jr. | 381/70 |
| 4,039,756 | 8/1977 | Burtschi | 381/70 |

FOREIGN PATENT DOCUMENTS 0106780  4/1984  European Pat. Off. ................ 623/9

Primary Examiner—Gene Z. Rubinson
Assistant Examiner—L. C. Schroeder
Attorney, Agent, or Firm—Harvey B. Jacobson

[57] ABSTRACT

A hand held housing encloses a battery powered sound generator from which an audible voice simulating tone is transmitted through a tube when a push button switch is depressed also causing illumination of an indicator lamp. The tube is displaceable relative to the housing between extended and retracted positions. In the extended position, the tube may be inserted into the mouth.

7 Claims, 6 Drawing Figures

VOICE SIMULATOR

BACKGROUND OF THE INVENTION

This invention relates to improvements in electronic voice simulating devices.

Electronic devices for simulating the acoustical output or audible tone generated by a human larynx from which speech is articulated in the oral cavity, are already known. Such devices are expensive, require precise adjustments and are intended exclusively for use as a medical prothesis.

It is therefore an important object of the present invention to provide a voice tone simulating device that is considerably less expensive and more convenient to use in artificially articulating speech, including use for amusement purposes as a toy.

SUMMARY OF THE INVENTION

In accordance with the present invention, all components of a signal tone generator, including a battery, oscillator, amplifier and transducer, are mounted in a common housing to which a tone transmitting tube is connected. The tube is displaceable relative to the housing between an extended position adapted to be inserted into the mouth of the user, and a retracted position. The open end portion of the tube from which the tone is emitted, is provided with a plurality of apertures for better distribution of sound within the oral cavity.

The housing enclosed signal tone generator is enabled by closing of a sidewall mounted push button switch that is normally held open under a spring bias. An indicator lamp on top of the housing is illuminated whenever the tone generator is operating to produce an output from the transducer.

These together with other objects and advantages which will become subsequently apparent reside in the details of construction and operation as more fully hereinafter described and claimed, reference being had to the accompanying drawings forming a part hereof, whrein like numerals refer to like parts throughout.

DETAILED DESCRIPTION OF PREFERRED EMBODIMENT

Figure 1:
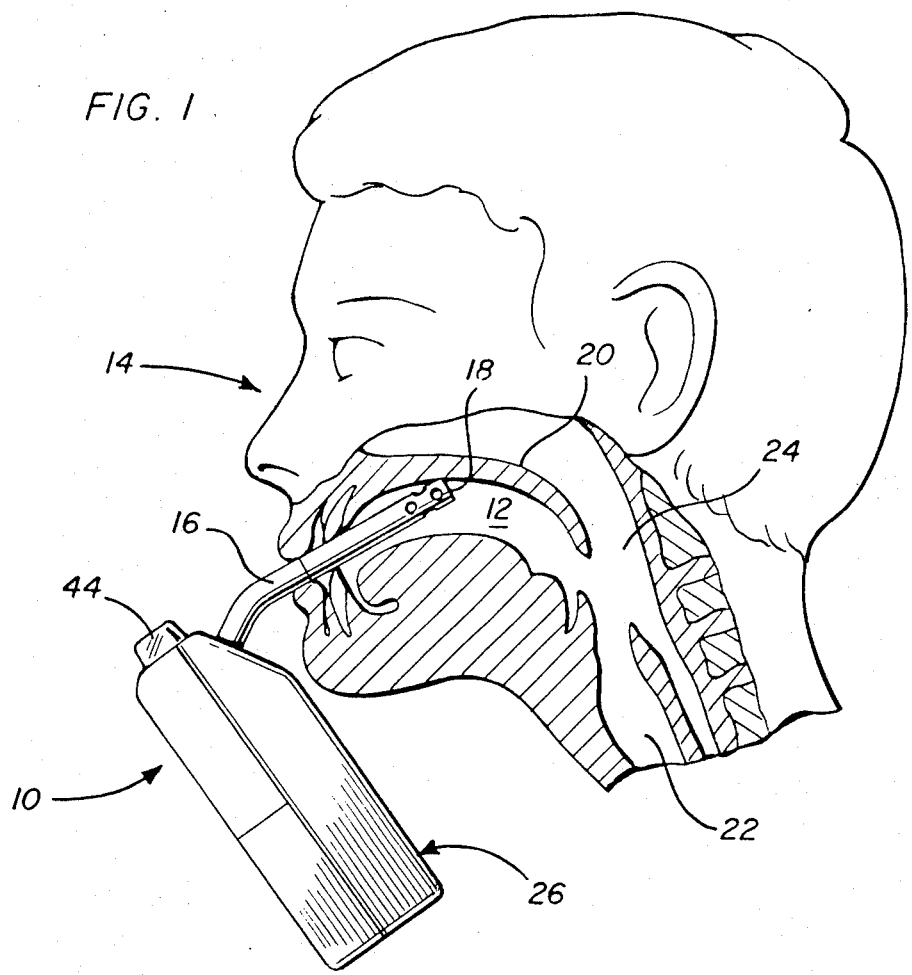
FIG. 1 is a simplified partial side section view of a human head with a device of the present invention inserted into the oral cavity.

Referring now to the drawings in detail, FIG. 1 shows the device of the present invention, generally referred to as reference numeral 10, inserted into the oral cavity 12 of a human head 14. More particularly, it is the audible tone transmitting conduit or tube 16 of the device 10 that is positioned in the mouth, with its opened end portion 18 disposed adjacent to the hard palate 20. By muscular control over the shape and size of the oral cavity, the sound emitted from the end portion 18 of the tube 16 will be transposed into intelligible speech since such sound substantially simulates the tone ordinarily produced by the natural larynx and transmitted therefrom through the esophagus 22 and pharynx 24 into the oral cavity 12. The larynx simulating tone is transmitted through the tube 16 from the housing 26 of the device 10. The housing is held in the hand externally of but adjacent to the mouth as shown.

Figure 2:
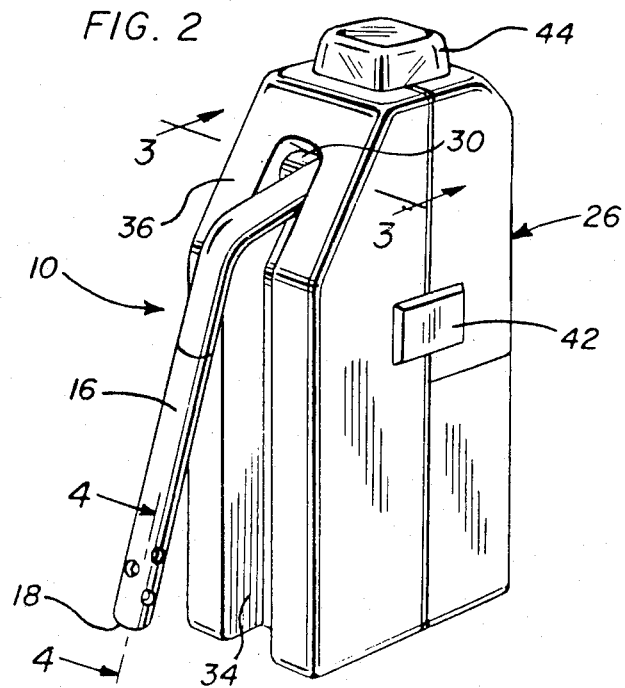
FIG. 2 is a perspective view of the device shown in FIG. 1.
Figure 3:
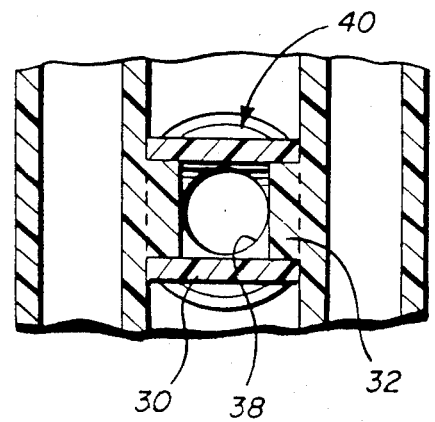
FIGS. 3 and 4 are enlarged partial section views taken substantially through planes indicated by section lines 3—3 and 4—4 in FIG. 2.
Figure 4:
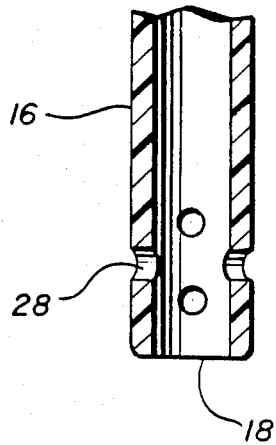

As more clearly seen in FIGS. 2, 3 and 4, the tube 16 includes a longer section extending at an obtuse angle to a shorter section, with the open end 18 remote from the shorter section. A plurality of sound distributing apertures 28 are formed in the tube adjacent the open end 18, while the opposite end of the tube has a transverse extension as more clearly seen in FIG. 3. The tube is pivotally connected to the housing by bearing supports 32, for example. The bearing supports project into the transverse extension 30. A groove 34 is formed in the front face portion 36 of the housing within which the tube is seated when retracted. The end of the tube 38 inside the housing is connected to an electromagnetic transducer 40 as shown in FIG. 3.

A push button switch 42 is mounted on one sidewall of the housing as shown in FIG. 2 while an indicator lamp 44 projects from the top wall. When the switch 42 is depressed against a spring bias, a signal tone is generated to produce an output from transducer 40 within the housing and the indicator lamp 44 is illuminated.

Figure 5:
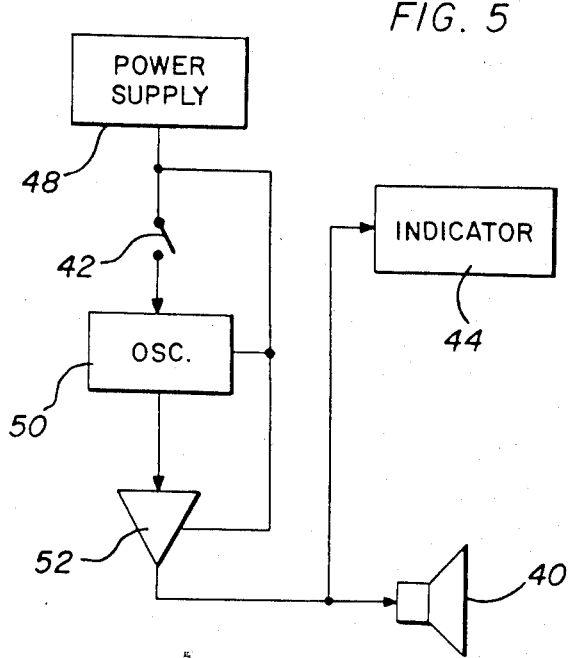
FIG. 5 is a block circuit diagram showing the signal tone generator associated with the present invention.

A signal tone generator 46 which drives the transducer 40 is diagrmamed in FIG. 5 and includes a power supply 48 connected to an oscillator 50 and an amplifier 52. The output of the oscillator operates the indicator 44 and is amplified by the amplifier 52 to drive the transducer 40. The oscillator is enabled by closing of switch 42 connecting the power supply thereto. Thus, operation of the device is manually controlled through switch 42 with the tube extended and inserted into the mouth. Each time the switch is depressed tones are emitted from the tube and the lamp 44 is illuminated within view of the user.

Figure 6:
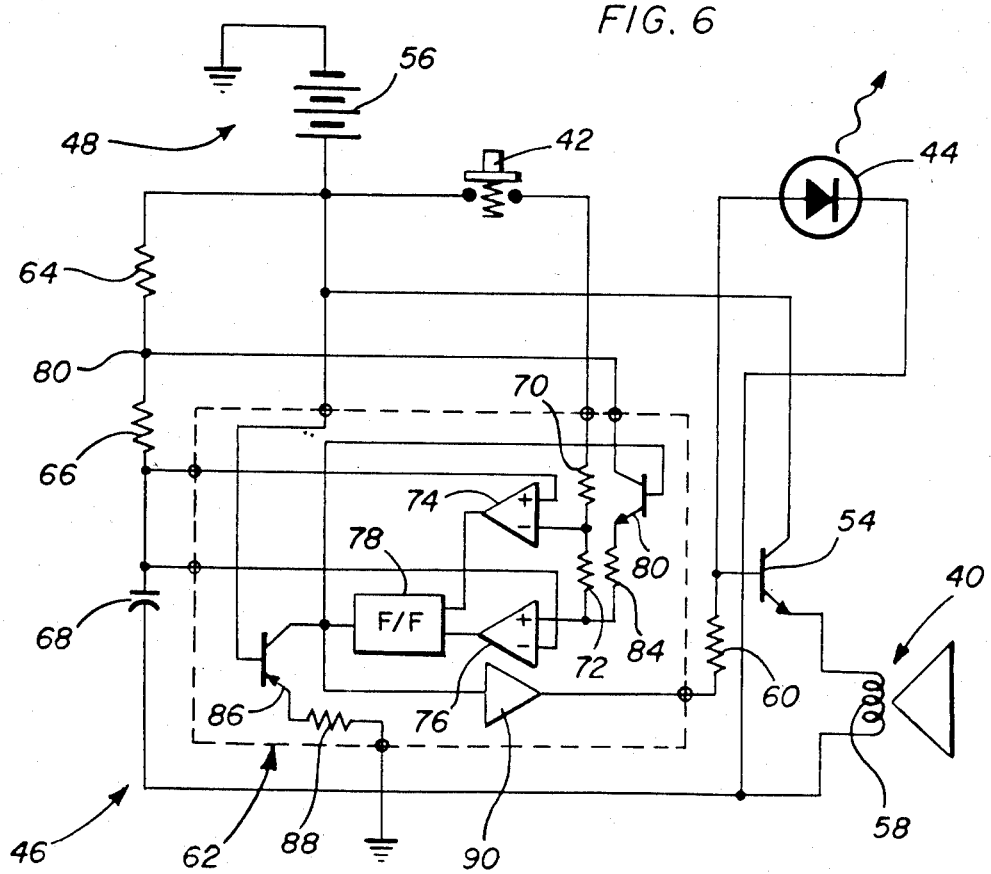
FIG. 6 is a circuit diagram showing the signal tone generator in greater detail.

FIG. 6 illustrates in greater detail the signal tone generator 46 which incorporates the oscillator 50 and amplifier 52. The amplifier 52 includes a transistor 54 having a collector directly connected to the output terminal of the power supply 48 in the form of a 9-volt battery 56. The output emitter of the transister 54 is connected to the inductance coil 58 of the transducer 40 to drive the transducer in response to a signal input applied to the base of transistor 54 through load resistor 60. The driving signal input to transistor 54 is generated by oscillator 50 in the form of a timer circuit 62 powered by battery 56 and operated in response to closing of switch 42. The oscillating output frequency of the circuit 62 is controlled by voltage dividing resistors 64 and 66 and capacitor 68 to which the indicator lamp 44 and transducer 40 are connected in parallel.

The timer circuit section 62 may be in the form of an integrated circuit chip in accordance with one embodiment of the invention having a circuit configuration as shown in FIG. 6. Battery voltage is applied through the switch 42 and voltage reducing resistors 70 and 72 to the inverting and non-inverting inputs, respectively, of a pair of operational amplifiers 74 and 76. The non-inverting input of amplifier 74 has a control potential maintained thereon by its connection to the battery source through the series connected resistors 64 and 66 and to the capacitor 68. The same control potential is also applied to the inverting input of amplifier 76. Thus, upon closing of switch 42, signal outputs of the amplifiers 74 and 76 cause a change in state of a control flip-flop 78, the output of which is connected to the base of a switching transistor 80. The transistor 80 is thereby switched on to conduct current from the junction 82 between resistors 64 and 66 through resistor 84 to the non-inverting input of amplifier 76. The amplifier 76 will accordingly cause the flip-flop to return to its previous state to cut off the transistor 80 and initiate another operational cycle at an oscillating frequency determined by capacitor 68 to which the inputs of amplifiers 74 and 76 are connected and the resistors 64 and 66 through which the capacitor 68 is charged from the battery 56.

The signal level of the oscillating output of flip-flop 78 is controlled by a transistor 86 having a base directly connected to the battery, a collecter connected to the output of flip-flop 78 and an emitter connected to ground through a reference resistor 88. The output of the flip-flop 78 and transistor 86 at its collector is applied to a power output amplifier 90 from which the signal output is transmitted through load resistor to lamp 44 and the input base of the signal amplifying transistor 54 as aforementioned.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A voice simulating device having a dc source of voltage, means connected to said source for generating a signal characteristic of the acoustical wave form produced by a human larynx, transducer means for reproducing said signal as an audible tone, amplifier means connecting said signal generating means to the transducer means for amplification of the signal reproduced by the transducer means and conduit means for transmitting the audible tone from the transducer means into a human oral cavity wherein the tone is adapted to be transposed into intelligible speech, the improvement comprising a housing enclosing the voltage source, the signal generating means, the transducer means and the amplifier means and means pivotally mounting the conduit means in the housing for displacement thereof between extended and retracted positions, said housing having a face portion from which the conduit means projects in the extended position and a groove formed within the face portion within which the conduit means is seated in the retracted position thereof.

2. The improvement as defined in claim 1 wherein said conduit means includes an elongated tube having opposite end portions, one of the end portions being connected to the transducer means internally of the housing, the other of the end portions being open externally of the housing and formed with a plurality of apertures therein and a transverse extension projecting from said one of the end portions into bearing relation to the pivotal mounting means.

3. The improvement as defined in claim 2 including an indicator lamp mounted on the housing and switch means connected to the voltage source for selectively operating the signal generating means and the indicator lamp.

4. The improvement as defined in claim 1 including an indicator lamp mounted on the housing and switch means connected to the voltage source for selectively operating the signal generating means and the indicator lamp.

5. A voice simulating device having a dc source of voltage, means connected to said source for generating a signal characteristic of the acoustical wave form produced by a human larynx, transducer means for reproducing said signal as an audible tone, and conduit means for transmitting the audible tone from the transducer means into a human oral cavity wherein the tone is adapted to be transposed into intelligible speech, and a housing enclosing the transducer means, the improvement comprising means operatively mounting the conduit means in the housing for displacement between extended and retracted positions relative to the housing.

6. The improvement as defined in claim 5 wherein said conduit means includes an elongated tube having opposite end portions, one of the end portions being connected to the transducer means internally of the housing, the other of the end portions being open externally of the housing.

7. The improvement as defined in claim 6 including a transverse extension of the tube projecting from said one of the end portions into bearing relation to the pivotal mounting means, said housing being formed with a groove within which the tube is seated in the retracted position of the conduit means.

* * * * *